United States Patent [19]
Giger et al.

[11] Patent Number: 5,849,345
[45] Date of Patent: Dec. 15, 1998

[54] CAROTENOID KETONES AND ESTERS

[75] Inventors: Alfred Giger, Möhlin; Werner Simon, Riehen, both of Switzerland

[73] Assignee: Roche Vitamins Inc., Parsippany, N.J.

[21] Appl. No.: 573,814

[22] Filed: Dec. 18, 1995

[30] Foreign Application Priority Data

Dec. 21, 1994 [EP] European Pat. Off. .............. 94810741
Nov. 24, 1995 [EP] European Pat. Off. .............. 95118525

[51] Int. Cl.$^6$ ...................................................... A23L 1/303
[52] U.S. Cl. ................................. 426/2; 426/72; 426/73; 426/635; 426/89; 585/351; 424/439
[58] Field of Search .................................. 426/2, 72, 73; 585/351, 89; 424/439

[56] References Cited

U.S. PATENT DOCUMENTS

| | | | |
|---|---|---|---|
| 3,321,315 | 5/1967 | Yokoyama . | |
| 3,932,546 | 1/1976 | Buchi | 260/666 |
| 3,989,757 | 11/1976 | Surmatis | 260/598 |
| 4,127,455 | 11/1978 | Schulz | 204/78 |
| 4,316,917 | 2/1982 | Antoshkiw | 426/73 |
| 4,522,743 | 6/1985 | Horn | 426/73 |
| 4,726,955 | 2/1988 | Horn | 426/73 |
| 4,992,282 | 2/1991 | Mehansho | 426/73 |
| 5,153,012 | 10/1992 | Ohtaka | 426/73 |
| 5,270,063 | 12/1993 | Wullschleger | 426/73 |
| 5,364,563 | 11/1994 | Cathrein | 426/73 |
| 5,437,880 | 8/1995 | Takaichi | 426/73 |
| 5,516,535 | 5/1996 | Heckert | 426/2 |
| 5,532,009 | 7/1996 | Fortier | 426/73 |
| 5,648,550 | 7/1997 | Brungger | 568/388 |

FOREIGN PATENT DOCUMENTS

| | | |
|---|---|---|
| 630578 | 12/1994 | European Pat. Off. . |
| 1224393 | 6/1960 | France . |

OTHER PUBLICATIONS

Ronneberg 1985 Phytochemistry vol. 24(2) 309–319.
P. Karrer et al., Helvetica Chimica Acta, vol. 27, pp. 1588–1589 (1944).
S. Hertzberg et al., Acta Chemica Scandinavica vol. 21, No. 1, pp. 15–41 (1967).
H. Rosenneberg et al., Phytochemistry, vol. 24, No. 2, pp. 309–319 (1985).
E. Jaeger et al., Eur. J. Med. Chem., vol. 28, No. 4, pp. 275–290 (1993).
E. Hawkins et al., Journal of the Chemical Society, p. 411 (1944).
Chemical Abstract No. 9731N.
Hughes, Use of the synthetic oxycarotenoids, β–apo–8'–cartenoic acid ethyl ester and citranaxanthin, in diets low in natural pigments to enhance egg yolk colour, Aust. J. Exp. Agric. vol. 25, pp. 41–46 (1985).
Aprin, et al, Recherches Chimiotaxinomiques Sur Les Champignons Fungal Carotenoids, Phytochemistry, vol. 6, pp. 995–1005 (1967).
M.J. Vacheron, et al, Etude Par Spectrometrie De Masse D'un Carotenoide Isole D'un Discomycete Plectania Coccinea, Phytochemistry, vol. 8, pp. 897–903 (1969).

*Primary Examiner*—Carolyn Paden
*Attorney, Agent, or Firm*—George W. Johnston; Dennis P. Tramaloni; Bruce A. Pokras

[57] ABSTRACT

New carotenoids of the formula

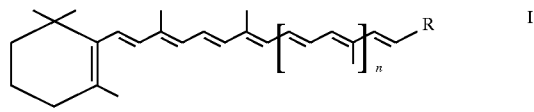

wherein R and n have the significances given herein, are useful for pigmenting the egg yolk, integuments and/or subcutaneous fat of poultry and the meat and/or integuments of fish and crustacea when included in the feed of the poultry, fish or crustacea. As well as such carotenoids and method of pigmenting the invention further embraces the pertinent carotenoid-enriched feed for poultry, fish or crustacea, the premixes for incorporation in such feeds and beadlets containing one or more of these carotenoids for incorporation in such premixes and the use of the carotenoids in the pigmenting method. The process of manufacturing such carotenoids, which more specifically may be designated as carotenoid ketones, monoesters and diesters, also represents an aspect of the invention.

30 Claims, No Drawings

CAROTENOID KETONES AND ESTERS

BACKGROUND OF THE INVENTION

It is well known that carotenoids are natural pigments which occur abundantly in the plant and animal kingdoms and which in some cases have also been produced by synthetic means. Further synthetically produced carotenoids do not appear to occur in nature. Many important carotenoids are employed as pigments in the food and feedstuff industries, e.g., for colouring egg yolk, poultry, fish and crustacea, notably in the cases of ethyl β-apo-8'-carotenoate, citranaxanthin, canthaxanthin and astaxanthin. For this purpose the carotenoid pigments are added to the animals' rations as a method of imparting an enhanced and aesthetically more acceptable visual impression of colour, be it in the animal integuments, such as the skin, shanks and beaks of poultry and the skin, scales and shells of fish and crustacea, as appropriate, subcutaneous fat of poultry and the meat of fish and crustacea, or in such animal products as eggs (yolk). The enhancement of pigmentation depends on the particular light-absorbing conjugated double bond system of the carotenoid concerned, the degree of ease with which the carotenoid is taken up into the animal body following consumption of the carotenoid-enriched feed (deposition rate) and the concentration of the carotenoid or any metabolites in the target animal body tissue or product, amongst many other factors. However, from a knowledge of the structure of the selected carotenoid it cannot be predicted how effectively it functions as a pigment in this area of application. A further factor involved is the stability of the carotenoid, e.g., towards atmospheric oxidation, light, temperature and dampness, in an animal feedstuff when stored under the normal conditions to which such a feedstuff is subjected.

With respect to poultry an acceptable level and quality of pigmentation is desired for the integuments of the birds destined for consumption and for egg yolk. The use of materials to enhance yolk colour, for example, is generally promoted because consumers prefer deeply (particularly rich golden yellow) pigmented yolks. The visual appearance is indeed an important factor in the assessment of quality. Broilers and ornamental birds, for example, are in many parts of the world more aesthetically acceptable if their integuments, particularly skin, shanks and beaks, in the case of broilers also their subcutaneous fat, and in the case of ornamental birds also their plumage, satisfy certain criteria of pigmentation. The need for supplementary pigmentation is especially prevalent today in view of the reduction of grass consumption with the modern methods of intensive poultry rearing, which involve the use of low fibre, high energy feeds, rendering difficult the production of well-pigmented poultry and egg yolks.

The pigmentation of fish meat and integuments, especially of various species of trout and salmon, and the meat and integuments of crustacea, e.g., crabs, lobsters and shrimps, is also well known to be achieved by feeding the fish and crustacea with carotenoid-enriched feed preparations with a view to rendering the edible products more attractive to consumers.

Moreover, alimentary products such as dairy products, e.g., butter and cheese, and such cosmetic products as lipsticks are known to be pigmentable by incorporation of carotenoids at a suitable stage of the pertinent production processes.

SUMMARY OF THE INVENTION

It has now been found that certain new carotenoids, as will be specified hereinafter, are effective as pigments in the above-indicated applications, or surprisingly are even more effective as such, than the carotenoids known to have been used hitherto for such purposes.

According to the present invention there are provided new carotenoids of the formula:

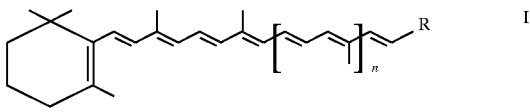

wherein
R is a group (a), (b) or (c)

 (a)

in which $R^1$ is $C_{1-6}$-alkyl or $C_{2-6}$-alkenyl,

 (b)

 (c)

in each of which $R^2$ is $C_{1-5}$-alkyl, and
n is zero or an integer 1 to 4,
with the proviso that when n is zero and R is a group (a), then $R^1$ is other than methyl.

The above and the hereinafter presented structural formulae are represented in the abbreviated manner, using simple lines, which is usual in carotenoid chemistry.

DETAILED DESCRIPTION OF THE INVENTION

In one aspect, the present invention comprises a carotenoid of the formula:

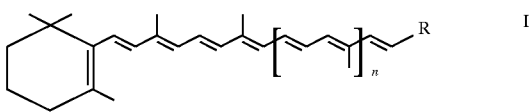

wherein
R is a group (a), (b) or (c)

 (a)

in which $R^1$ is $C_{1-6}$-alkyl or $C_{2-6}$-alkenyl

 (b)

 (c)

in each of which $R^2$ is $C_{1-15}$-alkyl, and
n is zero or an integer 1 to 4,
with the proviso that when n is zero and R is a group (a), then $R^1$ is other than methyl.

R is preferably group (a) or (b). When R is group (a), n is preferably an integer from 1 to 4, particularly 3 or 4, and $R^1$ is preferably $C_{1-6}$-alkyl, particularly methyl. The preferred compound when R is group (a) and n is 3 is 5,9,13, 18,22-pentamethyl-24-(2,6,6-trimethyl-1-cyclohexen-1-y)-3,5,7,9,11,13,15,17,19,21,23-tetracosaundecaen-2-one. The preferred compound when R is group (a) and n is 4 is 5,9,13,17,22,26-hexamethyl-28-(2,6,6-trimethyl-1-cyclohexen-1-yl)-3,5,7,9,11,13,15,17,19,21,23,25,27-octacosatridecaen-2-one [or (16'-torulyliden)acetone].

When R is group (b), n is preferably an integer from 1 to 4, particularly 3. $R^2$ is preferably methyl or pentadecyl. The preferred compounds when R is group (b) and n is 3 are 2'-dehydroplectaniaxanthin acetate and 2'-dehydroplectaniaxanthin palmitate.

In the scope of the present invention the term "$C_{1-6}$-alkyl group" or "$C_{2-6}$-alkenyl group" means straight-chain and branched groups having the recited number of carbon atoms such as, for example, methyl, ethyl, isopropyl and tert. butyl or, respectively, vinyl and 4-methyl-3-pentenyl. Similarly, the term "$C_{1-15}$-alkyl" means straight-chain and branched groups having the recited number of carbon atoms, and may be exemplified by the preferred groups methyl and pentadecyl.

The above compounds of the invention (and each later disclosed compound) encompass isomeric forms, e.g., optically active and cis/trans or E/Z isomers, as well as mixtures thereof, unless an isomeric form is specifically indicated. With respect to E/Z isomerism, the all-E isomers are preferred.

Specific examples of the new compounds of the invention are:

the total concentration of the carotenoid of the invention in the composition is in the range 0.1 ppm to 150 ppm based on the total weight of the composition. When the method of the invention is carried out with poultry it is especially preferred that the total concentration of the carotenoid of the invention in the composition be in the range from 0.25 ppm to 20 ppm based upon the total weight of said composition. When the method of the invention is carried out with fish or crustacea it is especially preferred that the total concentration of the carotenoid of the invention in the composition be in the range from 2.5 ppm to 150 ppm based upon the total weight of said composition.

For carrying out the method of the present invention, the carotenoid of the invention is applied via the poultry, fish or crustacea feed composition of the invention described herein, as appropriate, and in these circumstances the carotenoid responsible for the enhanced pigmentation is ingested by the pertinent animal in a natural manner.

A further aspect the present invention is directed to a feed composition for poultry, fish or crustacea comprising a poultry, fish or crustacea feed and a carotenoid of the invention, wherein said carotenoid is present in said feed composition in an amount effective to pigment the egg yolk, integuments and subcutaneous fat of the poultry or to pigment the meat and integuments of the fish and crustacea to which said feed composition is fed. The amount of the carotenoid of the invention in said feed composition is preferably in the range 0.1 ppm to 150 ppm based on the total weight of said feed composition. For a poultry feed, the amount of the carotenoid of the invention in the feed composition is particularly preferred to be in the range from 0.25 ppm to 20 ppm based upon the total weight of said feed 5,9,13,18,22-Pentamethyl-24-(2,6,6-trimethyl-1-cyclohexen-1-yl)-3,5,7,9,11,13,15,17,19,21,23-tetracosaundecaen-2-one

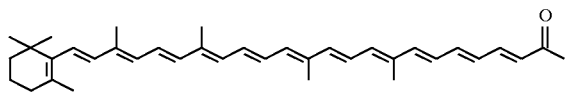

5,9,13,17,22,26-Hexamethyl-28-(2,6,6-trimethyl-1-cyclohexen-1-yl)- 3,5,7,9,11,13,15,17,19,21,23,25,27-octacosatridecaen-2-one [or (16'-torulenylidene)acetone]

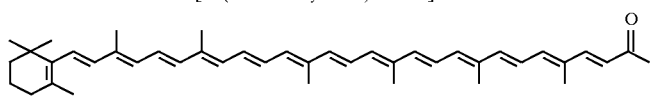

2'-Dehydroplectaniaxanthin acetate

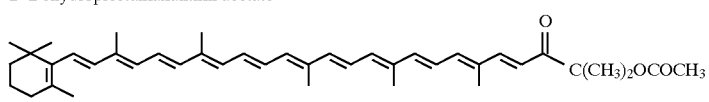

2'-Dehydroplectaniaxanthin palmitate

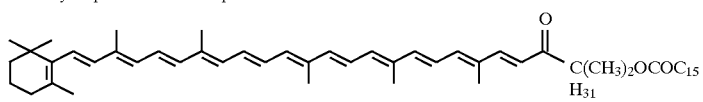

The present invention is also directed to a method of pigmenting the egg yolk, integuments and subcutaneous fat of poultry, and the meat and integuments of fish and crustacea, said method comprising feeding said poultry, fish or crustacea a feed composition comprising a feed for said poultry, fish or crustacea and a carotenoid of the invention wherein said composition is fed to said poultry, fish or crustacea in an amount effective to pigment the egg yolk, integuments and subcutaneous fat of said poultry or the meat and integuments of said fish or crustacea. It is preferred that composition. For a fish or crustacea feed, the amount of the carotenoid of the invention in the feed composition is particularly preferred to be in the range from 2.5 ppm to 150 ppm based upon the total weight of the feed composition.

The pertinent feed composition may also contain other carotenoids which themselves contribute to the normal pigmentation of egg yolk, integuments and subcutaneous fat of poultry and the meat and integuments of fish and crustacea.

The ingredients of the poultry, fish or crustacea feed useful for the feed composition of the invention are any conventional ingredients known in the art for the respective poultry, fish and crustacea feeds. The feed composition of the invention may also be produced by any conventional means, including, e.g., physical admixture, pelleting, extrusion, microencapsulation, spraying, etc., whereby at some stage during the production process one or more of the carotenoids of the invention are incorporated in the feed to produce the feed composition of the invention.

The conventional ingredients of poultry feed include, for example, wheat, maize, barley, sorghum, oats, rice and/or soybean meal, usually in ground or broken form, as appropriate, in major proportions (at least about 10 percent by weight in each case). Further ingredients in minor amounts (up to about 5 percent by weight, or in certain cases less than 1 percent by weight) include, for example, fish, meat and/or bone meal, wheat bran, straw, yeast, hydrolysed fat, tallow, lard, limestone, salt, methionine premix, mineral premix, vitamin premix and/or anticaking agent. Any poultry feed can be enriched with one or more of the carotenoids of the invention to afford a poultry feed composition of the present invention.

Typical fish or crustacea feed compositioins of the present invention include, apart from the added carotenoid(s) of the invention, fish meal, as the major source of proteins, wheat and bone meal, soybean meal, wheat flour, cooked starch, yeast, fish oil, soybean oil, soya lecithin, methionin, vitamins and minerals. The protein, lipids and carbohydrate content of such a feed is approximately 40–50%, 15–30% and 10% by weight, respectively.

The carotenoids of the invention are preferably prepared as a composition in beadlet form, which beadlets represent a further aspect of the present invention. The beadlets contain, apart from a carotenoid of the invention, a matrix of gelatin and carbohydrate, and one or more conventional anti-oxidants which are pharmaceutically acceptable for use in animal feeds, e.g., ethoxyquin and/or ascorbyl palmitate. The beadlets of the invention preferably contain a carotenoid of the invention in an amount of from 1 to 20 percent by weight of the beadlet. Beadlets containing carotenoids are conventional in the art, and the beadlets of the invention may be produced by any conventional means. Preferably, the beadlets are produced by the "starch-catch" method disclosed in U.S. Pat. No. 2,756,177. Additionally, the beadlets may be crosslinked for greater mechanical stability. Such crosslinking may be performed by any conventional means. The crosslinking method disclosed in U.S. Pat. No. 4,670,247 is preferred, but other means, e.g., those disclosed in U.S. Pat. Nos. 5,126,328, 5,153,177 and 5,356,636 may also be used.

The beadlets of the invention may be mixed into and form a part of a composition known in the art as a premix. A premix is a composition which when added to a poultry, fish or crustacea feed provides a combination of nutrients and pharmaceutically active substances for ingestion by said poultry, fish or crustacea. The premix of the invention contains a carotenoid of the invention and additional nutrients or pharmaceutically active substances, also possibly in the form of beadlets, which are used to supplement the conventional animal feed and produce the final feed composition. The premixes of the invention preferably contain a carotenoid of the invention in an amount of from 0.001 to 15 percent by weight of the premix. Premixes are formulated with combinations and amounts of nutrients and pharmaceutically active substances which are specific for the animal to which the final feed composition is to be fed. Nutrients include, but are not limited to, vitamins, minerals, and the like which are used to supplement the nutritional value of the feed. Pharmaceutically active substances include, but are not limited to, antibiotics, growth enhancement agents, and the like, which are advantageous to be included in the final feed composition.

The carotenoids of the invention may be produced by any conventional means. Preferably, the carotenoids of the invention in which R is a group (a) (which are collectively embraced by the general formula

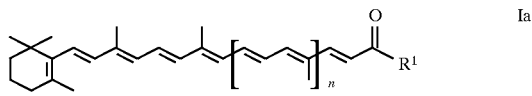

and may conveniently be designated as carotenoid ketones) are produced by (i) condensing the corresponding carotenal (carotenoid aldehyde) of the general formula

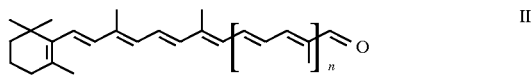

with the appropriate ketone of the general formula

(a Claisen-Schmidt condensation) or by (ii) reacting said carotenal with the appropriate alkanoyl- or alkenoylmethylenetriphenylphosphorane of the general formula

(a Wittig reaction).

Furthermore, those carotenoids of the the invention in which R is a group (b) [which are collectively embraced by the general formula

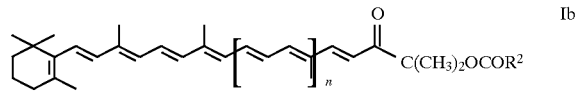

and may conveniently be designated as carotenoid monoesters] and the carotenoids of the invention in which R is a group (c) [which are collectively embraced by the general formula

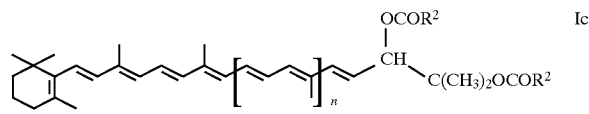

and may conveniently be designated as carotenoid diesters] are preferably produced by (iii) reacting the corresponding carotenoid alcohol or dialcohol, respectively, of the general formula

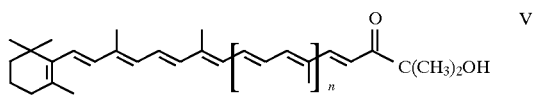

or

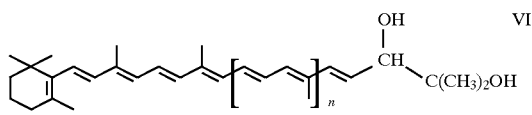

respectively, with the appropriate alkanoic acid of the general formula $R^2COOH$      VII or with a reactive derivative thereof.

The process of production of the carotenoids of the present invention according to the three variants (i), (ii) and (iii) hereinabove represents a further aspect of the present invention.

The Claisen-Schmidt condensation (i) is conveniently effected by reacting the carotenal with an excess of the ketone, optionally in an inert solvent or whereby the ketone itself can often serve as the solvent, at temperatures in the range 25–150° C., preferably 25–80° C., and in the presence of a base. If a solvent (additional to the ketone itself) is used, this must of course not be of a type which would react under the reaction conditions with the ketone or the base, and is preferably a lower alcohol, especially a $C_{1-4}$-alkanol, e.g., methanol, or a halogenated aliphatic hydrocarbon, especially methylene chloride.

The base can be inorganic or organic, and especially suitable ones are alkali metal hydroxides, e.g., sodium and potassium hydroxides, and alkali metal alkoxides, especially those derived from $C_{1-3}$-alkanols, such as sodium methoxide. If an alkali metal hydroxide is used, this may be introduced as an aqueous or alcoholic solution, whereby in the latter case the alcohol is suitably a $C_{1-3}$-alkanol. Especially preferred is potassium hydroxide in methanol. As regards the (excess) amount of ketone used in relation to the carotenal educt, there are preferably used at least 1.1 equivalents of ketone per equivalent of carotenal. The amount of base used is suitably from 0.2 to 5 equivalents per equivalent of carotenal. In general the reaction is completed within 1 to 24 hours.

The isolation and purification of the so produced carotenoid ketones of formula Ia can be carried out by conventional methods. Thus, the base can be neutralized by addition of an inorganic or organic acid to the post-reaction mixture, and the product can then be collected by filtration, washed with methanol and if necessary recrystallized. An alternative method comprises extracting the formed (alkali metal) salts from the post-reaction mixture with water and ether, distilling off the organic solvent from the organic phase containing the product or adding a further suitable solvent to said phase in order to precipitate out the product. As in the first-mentioned method the product can then be washed and/or recrystallized as necessary. The particular isolation method chosen will depend on the solvent used in the preparative reaction, and all procedures are well within the skills of the artisan. The second-mentioned method for producing the carotenoid ketones [the Wittig reaction, (ii)] is a standard method in carotenoid chemistry and can be effected analogously to the many well-documented examples of such a base-induced Wittig reaction of a carotenoid aldehyde and particularly acetylmethylene-triphenylphosphorane.

The starting materials used in the two process variants (i) and (ii), viz. of formulae II, III and IV, are either known compounds or can be produced by methods known per se, i.e., analogous to the methods for producing the known compounds. Amongst the known carotenals of formula II are β-apo-4'-carotenal and torularhodinaldehyde, i.e., of the formula II, wherein n is 3 or 4, respectively.

As a reactive derivative of the alkanoic acid of formula VII useful in the process variant (iii) there may be used the acid chloride or anhydride. If the alkanoic acid itself is used, it is preferred to conduct the esterification in the presence of a dehydrating agent such as N,N'-dicyclohexylcarbodiimide. In either case it is furthermore preferred to conduct the esterification under basic conditions, i.e., in the presence of an added base, e.g., pyridine (which also simultaneously acts as solvent) or 4-dimethylaminopyridine, and indeed such esterification procedures are essentially well known to persons skilled in the art.

A particularly preferred method of producing the carotenoid monoacetates (i.e. the carotenoid esters of formula Ib in which $R^2$ is methyl) involves using acetic anhydride as the reactive derivative of acetic acid and conducting the esterification in a slightly basic organic solvent, especially pyridine, at temperatures in the range from about 50° C. to about 75° C. The exclusion of air, conveniently by conducting the reaction under an atmosphere of inert gas, e.g., argon, is recommended. Isolation and purification of the product is conveniently effected by hydrolysing the post-reaction mixture with an ice/water mixture, extracting with diethyl ether, washing the organic phase with dilute sulphuric acid and water, drying it, e.g., over anhydrous sodium sulphate, filtering, and evaporating off the solvent, after which the so-isolated product can be purified by chromatography and recrystallization.

A particularly preferred method of producing those carotenoid monoesters of formula Ib in which $R^2$ is a $C_{2-15}$ alkyl group, i.e., ethyl to pentadecyl, and the carotenoid diesters (formula Ic) involves reacting the pertinent alcohol or dialcohol of formula V or VI, respectively, with an excess of the appropriate alkanoic acid in an aprotic solvent, especially toluene, in the presence of 4-dimethyl-aminopyridine as a base and of N,N'-dicyclohexylcarbodiimide as a dehydrating agent, at temperatures in the range from about 50° C. to about 75° C. As in the case of the acetate, the reaction is advisably effected under an inert gas, e.g., argon, and the isolation and purification is also conveniently effected analogously, whereby in this case extra toluene rather than diethyl ether is preferably added to the post-reaction mixture and to extract the product.

In general, an excess amount of the alkanoic acid of formula VII relative to the amount of carotenoid alcohol or dialcohol of formula V or VI, respectively, is used in both methods, whereby clearly a greater excess (preferably 8–10 molar) is required for the production of the carotenoid diesters of formula Ic than for that (preferably 4–5 molar) of the carotenoid monoesters of formula Ib.

The starting materials used in this process variant (iii), viz of formulae V, VI, VII, are either known compounds or can be produced by methods known per se, i.e., analogous to the methods for producing the known compounds. Amongst the known compounds of formulae V and VI are 2'-dehydroplectaniaxanthin and its reduction product, racemic (rac.) plectaniaxanthin, respectively.

The invention is illustrated by the following Examples:

EXAMPLE 1

Preparation of 5,9,13,18,22-pentamethyl-24-(2,6,6-trimethyl-1-cyclohexen-1-yl)-3,5,7,9,11,1 3,15,17,19,21,23-tetracosaundecaen-2-one 47,37 ml of methanolic potassium hydroxide solution (11,37%, 96 mmol KOH), 300 ml of acetone, 23,56 g β-apo-4'-carotenal (98.4% purity, 48 mmol) and 220 ml of methylene chloride are introduced at room temperature under an atmosphere of argon into a 750 ml sulphonation flask fitted with a stirrer and a thermometer. The mixture is stirred for 20 hours at 25° C. After completion of the resulting reaction of the carotenal with acetone the suspension so formed is transferred to a rotary evaporator and concentrated to dryness.

For purification the residue obtained in the previous (reaction) stage is dissolved in 600 ml of methylene chloride and the resulting solution added dropwise within 40 minutes to 400 ml of boiling methanol contained in a 1.5 l sulphonation flask fitted with a stirrer, thermometer, dropping funnel and distillation column. The azeotropic mixture of methanol and methylene chloride is distilled off continously, and this distillation is continued to a final volume of 300 ml and sufficient methanol then added continuously to maintain this volume. After cooling the resulting suspension to 0° C. with an ice bath the crystals are filtered off and washed with methanol.

The crystal are purified a further two times by analogous methanol/methylene chloride exchange distillation.

The yield of 5,9,13,18,22-pentamethyl-24-(2,6,6-trimethyl-1-cyclohexen-1-yl)-3,5,7,9,11,13,15,17,19,21,23-tetracosaundecaen-2-one obtained in this way is 21,86 g (85.7% theoretical yield; 97.5% purity acc. HPLC). The product is in the form of dark red crystals.

$^1$H-NMR [$CDCl_3$; tetramethylsilane (TMS) as internal standard]: δ=1.03 ppm (s, 6H), 1.45–1.48 ppm (m, 2H), 1.58–1.64 ppm (m, 2H), 1.72 ppm (s, 3H), 1.91–2.02 ppm (m, 15H), 2.30 ppm (s, 3H), 6.11–6.70 ppm (m, 16H), 7.21+7.24 ppm (d, 1H).

EXAMPLE 2

Preparation of (16'-torulenylidene)acetone 20.0 g (36.4 mmol) of torularhodinaldehyde are slurried under argon with 400 ml of acetone in a 750 ml sulphonation flask fitted with a stirrer and a thermometer. To the stirred slurry at 40° C. are added within 3 minutes 35.1 ml of methanolic potassium hydroxide solution (11.66% w/v, 72.9 mmol KOH), and the mixture is stirred at 40° C. for 2 ¾ hours. Then 8.3 ml (145.8 mmol) of glacial acetic acid are added to neutralize the flask contents, followed rapidly by 200 ml of propanol through a dropping funnel. The temperature of the heating source (oil bath) is raised and the acetone distilled off, during which 400 ml of propanol are added dropwise. Altogether 600 ml of solvent are distilled off, and during the course of the azetropic distillation the internal temperature of the reaction mixture rises from 67 to 98° C., and the head temperature from 60 to 94° C. After 2 ½ hours of such solvent exchange distillation the mixture is cooled to room temperature, stirred for a further hour and the resulting crystal slurry then filtered. The crystals are washed twice with 100 ml, total 200 ml, of methanol and then dried at 500° C. for about 16 hours in an evacuated drying cabinet.

For purification the 17.35 g of black crystals obtained in the previous (reaction) stage are slurried with 200 ml of isopropanol in a 350 ml sulphonation flask. The slurry is then stirred and heated to reflux temperature (82° C.) with an oil bath. After an hour's stirring at this temperature, the slurry is cooled to room temperature with a water bath, stirred for a further hour and filtered. The collected black crystals are washed twice with 40 ml, total 80 ml, of isopropanol and then returned to the sulphonation flask and once again heated in 200 ml of isopropanol at reflux temperature for one hour. As before, the slurry is cooled to room temperature, stirred a further hour, filtered and the crystals washed with 80 ml of isopropanol in two portions. Then the crystals are dried at 50° C. for about 16 hours in an evacuated drying cabinet. There are obtained in this way 16.71 g (96.3% theoretical yield) of (16'-torulenylidene)acetone in the form of black crystals.

$^1$H-NMR ($CDCl_3$; TMS as internal standard): δ=1.04 ppm (s, 6H), 1.45–1.48 ppm (m, 2H), 1.60–1.63 ppm (m, 2H), 1.72 ppm (s, 3H), 1.95–2.02 ppm (t, 3H), 2.30 ppm (s, 3H), 6.14–6.70 ppm (m, 19H), 7.20–7.29 ppm (m, 1H).

EXAMPLE 3

Preparation of 15-Apo-β-carotenylideneacetone 30 g (105.6 mmol) of vitamin A aldehyde, 200 ml of acetone and 400 ml of n-heptane are introduced at room temperature under an atmosphere of argon into a 750 ml sulphonation flask fitted with a stirrer, a condenser, a dropping funnel and a thermometer. Within 60 minutes a solution of 2 g (50 mmol) of sodium hydroxide in 50 ml of ethanol is added dropwise, during which the temperature rises from 14.5° C. to about 20° C. Using an ice bath the temperature is maintained at 20° C. while the reaction mixture is stirred for 6 hours. Then 6.4 ml (50 mmol) of acetic acid are added within about a minute, and the temperature rises to about 280° C. Cooling is applied to prevent the temperature from exceeding 28° C.

For the isolation and purification of the product 200 ml of water are added to the flask contents and the aqueous mixture is transferred to a separating funnel together with 100 ml of n-heptane rinsings. The heptane layer is separated off, washed three times with 100 ml of water in each case and the combined aqueous phases are extracted three times with 50 ml of n-heptane in each case. Then the combined heptane phases are evaporated under reduced pressure to a volume of about 150 ml and the concentrate is stored under cooling (refrigerator). After seeding with crystals of previously produced product the so-produced 15-apo-β-carotenylideneacetone crystallizes out. This is filtered off, washed portionwise with cold n-heptane, and the crystallisate (12.18 g) finally dried at about 40° C./20mbar.

$^1$H-NMR($CDCl_3$; TMS as internal stardard): δ=1.03 ppm (s, 6H), 1.46–1.49 ppm (m, 2H), 1.60–1.63 ppm (m, 2H), 1.72 ppm (s, 3H), 2.0–2.03 ppm (m, 5H), 2.08 ppm (s, 3H), 2.29 ppm (s,3H), 6.12–6.28 ppm (m, 5H), 6.34+6.38 ppm (d, 1H), 6.82–6.89 ppm (m, 1H), 7.52–7.59 ppm (m, 1H).

EXAMPLE 4

Preparation of 12'-apo-β-carotenylideneacetone 35.06 g (100 mmol) of β-apo-12'-carotenal in 600 ml of acetone are introduced at room temperature under an atmosphere of argon into a 1.5 l sulphonation flask fitted with a stirrer, a condenser, a dropping funnel and a thermometer. Within 60 minutes a solution of 2 g (50 mmol) of sodium hydroxide in 50 ml of ethanol is added dropwise, during which the temperature rises from 230° C. to about 30° C. The reaction mixture is then stirred at about this temperature for three hours, after which 6.4 ml (50 mmol) of acetic acid are added within about 1 minute, causing the temperature to rise to about 26° C.

For the isolation and purification 400 ml of water are added and the contents of the flask together with 400 ml of methylene chloride rinsings are transferred to a separating funnel. The methylene chloride layer is separated off, washed three times with 50 ml of water in each case and the combined aqueous phases are extracted three times with 50 ml of methylene chloride in each case. Then the combined methylene chloride phases are evaporated under reduced pressure to an oil.

The oil resulting from the above-described extraction and evaporation operations is dissolved in 200 ml of methylene chloride, and the solution is diluted with 400 ml of n-hexane and then distilled at a bath temperature of 35° C. and under a reduced pressure of about 580 mbar to remove the methylene chloride. To the resulting concentrate, weighing about 80 g, are added a further 300 ml of n-hexane, and the whole is distilled at 35° C./390 mbar to afford a concentrate weighing about 100 g. This is cooled in a refrigerator, resulting in precipitation of crystals of the desired product 12'-apo-β-carotenylideneacetone. After being filtered off, the crystals are washed portionswise with 100 ml of n-hexane under ice bath-cooling and then dried at about 40° C./20 mbar. The yield of 12'-apo-β-carotenylideneacetone is 9 g.

¹H-NMR(CDCl₃; TMS as internal stardard): δ=1.03 ppm (s, 6H), 1.45–1.48 ppm (m, 2H), 1.59–1.65 ppm (m, 2H), 1.72 ppm (s, 3H), 1.93 ppm (s, 3H), 1.98–2.04 ppm (m, 8H), 2.30 ppm (s, 3H), 6.12–6.37 ppm (m, 6H), 6.54–6.64 ppm (m, 2H), 6.70–6.84 (m, 2H), 7.20+7.24 ppm (d, 1H).

EXAMPLE 5

Preparation of 1',2'-dihydro-17'-nor-beta-χ-caroten-2'-one 9.92 g (20 mmol) of β-apo 4'-carotenal are suspended in 50 ml of n-propanol under argon in a 200 ml sulphonation flask fitted with a stirrer, a condenser and a thermometer. Then 3.6 ml (40 mmol) of 2-butanone and 7.4 ml of 50% aqueous potassium hydroxide solution (100 mmol KOH) are added by pipette to the suspension. The temperature of the mixture rises from about 20° C. to about 26° C. on adding the base. The resulting dark violet suspension is then heated to 80° C. with an oil bath, and the mixture is stirred at this temperature for a further 2.5 hours, with thin layer chromatographic and HPLC control of the progress of the reaction. To the resulting red-brown suspension are then added 70 ml of water, and the mixture is stirred at 80° C. for a further hour. After being subsequently cooled down to about 25° C. using a water bath the reaction mixture is stirred for a further 30 minutes.

To isolate and purify the product, the crystals are filtered off from the suspension through a slotted glass filter with filter paper, then pressed firmly on the filter before washing in turn with two 50 ml amounts of n-propanol and three 50 ml amounts of water under suction. Between washing and filtering operations the crystal cake is firmly pressed on the filter. The so-collected and washed crystals are finally dried in an evacuated drying cabinet at 50° C. for about 16 hours. In this way there are obtained 10.3 g (95.9% theoretical yield) of 1',2'-dihydro-17'-nor-beta-χ-caroten-2'-one as violet crystals.

¹H-NMR(CDCl₃; TMS as internal stardard): δ=1.03 ppm (s, 6H), 1.12–1.15 ppm (t, 3H), 1.45–1.48 ppm (m, 2H), 1.60–1.63 ppm (m, 2H), 1.72 ppm (s, 3H), 1.95–2.04 ppm (m, 17H), 2.59–2.64 ppm (q, 2H), 6.15–6.70 ppm (m, 16H), 7.25+7.29 ppm (d, 1H)

EXAMPLE 6

Preparation of (all-E)-2,6,10,14,19,23-hexamethyl-25-(2,6,6-trimethyl-cyclohex-1-enyl)-pentacosa-4,6,8,10,12,14,16,18,20,22,24-undecaen-3-one In a 200 ml sulphonation flask fitted with a stirrer, a dropping funnel and a thermometer there are introduced under an atmosphere of argon 4.96 g (10 mmol) of β-apo-4'-carotenal and 100 ml of 3-methyl-2-butanone, whereupon these components are stirred to a suspension. The resulting red, thin suspension is then warmed to 40° C. with stirring, and 9.35 ml of 12% w/v methanolic potassium hydroxide solution (20 mmol KOH) are added dropwise within 4 minutes. The reaction mixture is stirred at about 40° C. for 2.75 hours, after which 1.14 ml of acetic acid (20 mmol CH₃COOH) are added, and the whole is cooled to about 2° C. using an ice/water bath and stirred at this temperature for about 30 minutes.

To isolate and purify the product the contents of the flask are filtered through a slotted glass filter with filter paper and the so-collected crystals washed in succession with two 25 ml amounts of methanol and three 25 ml amounts of water. Between washing and filtering operations the crystal cake is pressed firmly on the filter. The so-collected and washed crystals are finally dried in an evacuated drying cabinet at 50° C. for about 16 hours. In this way there are obtained 4.32 g (76.3% theoretical yield) of (all-E)-2,6,10,14,19,23-hexamethyl-25-(2,6,6-trimethyl-cyclohex-1-enyl)-pentacosa- 4,6,8,1 0,12,14,16,1 8,20,22,24-undecaen-3-one as copper-red, glistening crystals.

¹H-NMR(CDCl₃; TMS as internal stardard): δ=1.03 ppm (s, 6H), 1.14+1.16 ppm (d, 6H), 1.45–1.48 ppm (m, 2H), 1.57–1.63 ppm (m, 2H), 1.72 ppm (s, 3H), 1.96–2.02 ppm (m, 17H), 2.82–2.92 ppm (m, 1H), 6.10–6.70 ppm (m, 16H), 7.31+7.34 ppm (d, 1H).

EXAMPLE 7

Preparation of (all-E)-2,2,6,10,14,19,23-heptamethyl-25-(2.6,6-trimethyl-cyclohex-1-enyl)-pentacosa-4.6,8,10,12,14,16,1 8,2022,24-undecaen-3-one In a 200 ml sulphonation flask fitted with a stirrer, a dropping funnel and a thermometer there are introduced under an atmosphere of argon 4.96 g (10 mmol) of β-apo-4'-carotenal and 100 ml of 3,3-dimethyl-2-butanone, whereupon these components are stirred to a suspension. The resulting red, thin suspension is then warmed to 40° C. with stirring, and 9.35 ml of 12% w/v methanolic potassium hydroxide solution (20 mmol KOH) are added dropwise within 4 minutes. The reaction mixture is stirred for 4 hours at about 40° C. and for 1 hour at about 60° C., after which 1.14 ml of acetic acid (20 mmol CH₃COOH) are added, and the whole is cooled to about 2° C. using an ice/water bath and stirred at this temperature for about 30 minutes.

To isolate and purify the product the contents of the flask are filtered through a slotted glass filter with filter paper and the so-collected crystals washed in succession with two 25 ml amounts of methanol and three 25 ml amounts of water. Between washing and filtering operations the crystal cake is pressed firmly on the filter. The so-collected and washed crystals are finally dried in an evacuated drying cabinet at 50° C. for about 16 hours. In this way there are obtained 4.25 g (73.2% theoretical yield) of (all-E) 2,2,6, 10,14,1 9,23-heptamethyl-25-(2,6,6-trimethyl-cyclohex-1-enyl)-pentacosa-4,6,8,1 0,12,14,16,1 8,20,22,24-undecaen-3-one as violet, glistening crystals.

¹H-NMR(CDCl₃; TMS as internal stardard): δ=1.03 ppm (s, 6H), 1.19 ppm (s, 9H), 1.45–1.48 ppm (m, 2H), 1.57–1.66 ppm (m, 2H), 1.72 ppm (s, 3H), 1.97–2.03 ppm (m, 17H), 6.11–6.73 ppm (m, 16H), 7.38+7.42 ppm (d, 1H).

EXAMPLE 8

Preparation of (all-E)-2,7,11,15,20,24-hexamethyl-26-(2,6,6-trirnethyl-cyclohex-1-enyl)-hexacosa-5,7,9,11,13,15,17,19,21,23,25-undecaen-4-one In a 200 ml sulphonation flask fitted with a stirrer, a dropping funnel and a thermometer there are introduced under an atmosphere of argon 4.96 g (10 mmol) of β-apo-4'-carotenal and 100 ml of methyl isobutyl ketone, whereupon these components are stirred to a suspension. The resulting red, thin suspension is then warmed to 40° C. with stirring, and 9.35 ml of 12% w/v methanolic potassium hydroxide solution (20 mmol KOH) are added dropwise within 4 minutes. The reaction mixture is stirred at about 40° C. for 1.5 hours, after which 1.14 ml of acetic acid (20 mmol CH₃COOH) are added, and the whole is cooled to about 2° C. using an ice/water bath and stirred at this temperature for about 30 minutes.

To isolate and purify the product the contents of the flask are filtered through a slotted glass filter with filter paper and the so-collected crystals washed in succession with two 25 ml amounts of methanol and three 25 ml amounts of water. Between washing and filtering operations the crystal cake is pressed firmly on the filter. The so-collected and washed crystals are finally dried in an evacuated drying cabinet at 50° C. for about 16 hours. In this way there are obtained 5.64 g (97.2% theoretical yield) of (all-E)-2,7,11,1 5,20,24- hexamethyl-26-(2,6,6-trimethyl-cyclohex-1-enyl)-hexacosa-5,7,9,11,13,15,17,19,21,23,25-undecaen-4-one as copper-red crystals.

$^1$H-NMR(CDCl$_3$; TMS as internal stardard): δ=0.95+0.97 ppm (d, 6H), 1.04 ppm (s, 6H), 1.45–1.48 ppm (m, 2H), 1.60–1.63 ppm (m, 2H), 1.72 ppm (s, 3H), 1.95–2.04 ppm (m, 17H), 2.10–2.25 ppm (m, 1H), 2.45+2.47 ppm (d, 2H), 6.11–6.70 ppm (m, 16H), 7.24+7.27 ppm (d, 1H).

EXAMPLE 9
Preparation of (all-E)-2,9,13,17,22,26-hexamethyl-28-(2,6,6-trimethyl-cyclohex-1-enyl)-octacosa-2,7,–9,11,13,15,17,19,21,23,25,27-dodecaen-6-one In a 750 ml sulphonation flask fitted with a stirrer, a dropping funnel and a thermometer there are introduced under an atmosphere of argon 29.76 g (60 mmol) of β-apo-4'-carotenal and 400 ml of 6-methyl-5-hepten-2-one, whereupon these components are stirred to a suspension. The resulting dark red suspension is then warmed to 40° C. with stirring, and a solution of 7.92 g (120 mmol) of potassium hydroxide in 50 ml of methanol is added dropwise within 4 minutes. The reaction mixture is stirred at about 40° C. for 4.25 hours, after which 6.86 ml of acetic acid (120 mmol CH$_3$COOH) are added, and the whole is cooled to about 2° C. using an ice/water bath and stirred at this temperature for about 30 minutes.

To isolate and purify the product the contents of the flask are filtered through a slotted glass filter with filter paper and the so-collected crystals washed in succession with two 150 ml amounts of methanol and three 150 ml amounts of water. Between washing and filtering operations the crystal cake is pressed firmly on the filter.

The so-collected and washed crystals are finally dried in an evacuated drying cabinet at 50° C. for about 16 hours. In this way there are obtained 24.36 g (66.9% theoretical yield) of (all-E)-2,9,13,17,22,26-hexamethyl-28-(2,6,6-trimethyl-cyclohex-1-enyl)-octacosa-2,7,9,11,13,15,17,19,21,23,25,27-dodecaen-6-one as violet, glistening crystals.

$^1$H-NMR(CDCl$_3$; TMS as internal stardard): δ=1.03 ppm (s, 6H), 1.45–1.48 ppm (m, 2H), 1.59–1.72 ppm (m, 11H), 1.94–2.04 ppm (m, 17H), 2.30–2.35 ppm (q, 2H), 2.59–2.63 ppm (t, 2H), 5.10–5.14 ppm (t, 1H), 6.15–6.70 ppm (m, 16H), 7.24+7.30 ppm (d, 1H).

EXAMPLE 10
Preparation of 2'-dehydroplectaniaxanthin acetate

A mixture of 556 mg (1.0 mmol) of 2'-dehydroplectaniaxanthin, 20 ml (25.7 mmol) of pyridine and 10 ml (10.5 mmol) of acetic anhydride are heated with an oil bath at 75° C. with stirring for 17 hours and then cooled to room temperature. To the mixture are then added 50 ml of absolute diethyl ether and in portions thereafter 20 g of ice, and the whole is stirred at room temperature for 40 minutes. To isolate and purify the product the aqueous ethereal mixture is extracted with further diethyl ether and the ether phase washed in turn with five 50 ml portions of cold 3N sulphuric acid, 100 ml of ice water, a further 100 ml of ice water containing 5 ml of saturated sodium bicarbonate solution and two 100 ml portions of ice water. The aqueous phase is neutral at this stage. Then the ethereal phase is dried over anhydrous sodium sulphate, filtered and the solvent evaporated off at 35° C. under reduced pressure (water jet vacuum). Finally the product is dried under high vacuum.

In this way there are obtained 641 mg of very dark red crystals. A chromatographic purification through a silica gel column affords 560 mg of product. On submitting this to a recrystallization from a methylene chloride/n-hexane mixture and to stirring over about 16 hours at 40° C. there are finally obtained 141 mg of 2'-dehydro-plectaniaxanthin acetate of 99.7% purity according to HPLC as dark red crystals, m.p. 177–178° C. UV/VIS (n-hexane+1% methylene chloride+1% ethanol): λmax=493 nm; A$^1_1$=2476; ε=150500.

EXAMPLE 11
Preparation of 2'-dehydroplectaniaxanthin palmitate

A solution of 566 mg (1.0 mmol) of 2'-dehydroplectaniaxanthin in 50 ml of absolute toluene is treated with a whole portion of 1126 mg (4.4 mmol) of palmitic acid and 390 mg (3.2 mmol) of 4-dimethylaminopyridine, whereafter the reaction mixture is warmed to an internal temperature of 60–62° C. 906 mg (4.4 mmol) of N, N'-dicyclohexylcarbodiimide dissolved in 10 ml of absolute toluene are then added, and the mixture in then maintained at 60–62° C. for 44 hours.

After cooling the mixture to 5° C. it is extracted with toluene, and the toluene phase is washed in turn with five 50 ml portions of ice water, 50 ml of ice water containing 1 ml of IN sulphuric acid and two 50 ml portions of ice water. Then the organic phase is dried over anhydrous sodium sulphate and the solvent removed by evaporation at 35° C. under a water jet vacuum. The resulting very dark red oil is chromatographed with n-hexan/diethyl-ether (9:1) through a silica gel column, and the collected fractions are evaporated to dryness under reduced pressure (water jet vacuum) at 35° C. The residue is recrystallized from methylene chloride/ethanol. After being stirred at 4° C. for about 16 hours the crystals are dried under high vacuum at 30° C., affording 285 mg of 2'-dihydroplectaniaxanthin palmitate as very dark red crystals, m.p. 124–126° C. According to HPLC the purity is 95.6%.

UV/VIS (n-hexane+2% methylene chloride): λmax=493 nm; A$^1_1$=1686; ε=135700.

EXAMPLE 12
Preparation of racemic plectaniaxanthin and therefrom of rac. plectaniaxanthin diacetate 70.0 g (123 mmol) of 2'-dehydroplectaniaxanthin are dissolved in 2000 ml of methylene chloride and 500 ml of methanol. At 16–18° C. 4.70 g (123 mmol) of sodium borohyride are added in portions, and the mixture is stirred for 1.5 hours at room temperature. The resulting solution is then cooled to 10° C., and approx. 150 ml of 1N sulphuric acid are added at such a rate that the temperature is maintained between 10° and 15° C. until a pH between 7 and 8 is obtained. The resulting mixture is then extracted three times with 500 ml of methylene chloride in each case. The organic layer is washed several times with 500 ml of ice-water, then dried over anhydrous sodium sulphate and evaporated at 35° C. using a water jet vacuum. The resulting crystalline mass is stirred with 1500 ml of diethyl ether and the resulting suspension filtered. In this way there are obtained 12.2 g (HPLC purity 97%) of racemic plectaniaxanthin crystals.

The filtrate is suspended in 700 ml of methanol and the suspension is boiled at reflux temperature for 16 hours. The methanol is then removed by evaporation at 35° C. under reduced pressure using a water jet vacuum. Crystallization of the residue from methylene chloride/n-hexane at 4° C. over about 16 hours gave an additional 27.5 g of rac. plectaniaxanthin as reddish brown crystals, m.p. 170–172° C. According to HPLC the purity is 99%.

UV/VIS (n-hexane+1% chloroform+1% ethanol): λmax= 447 nm (A$^1_1$=1996, ε=115800), 473nm (2932, 170100), 505nm (2590, 150300).

7.73 g (17.6 mmol) of rac. plectaniaxanthin (98.9% purity according to HPLC) are suspended in 500 ml of toluene.

Then 16.61 g (136 mmol) of 4-dimethylaminopyridine are added in one portion. After approx. 10 minutes stirring 8.17 ml (136 mmol) of acetic acid are added in one portion followed by a solution of 28.05 g (136 mmol) of N,N'-dicyclohexylcarbodiimide in 60 ml of toluene during 15–20 minutes. The resulting solution is stirred for 24 hours at room temperature. Then the solution is cooled down to -10° C. while stirring for 10 minutes. The precipitated urea is filtered off and washed twice with 30 ml of cold toluene in each case. The toluene layer is treated while stirring at 0° C. with 250 ml of deionized ice-water and then with 100 ml of 3N sulphuric acid. After stirring for 5 minutes the toluene layer is separated off and washed 7 times with 200 ml of deionized water in each case. Then the toluene layer is dried over anhydrous sodium sulphate and concentrated at 40° C. under reduced pressure (rotary evaporator) and then under high vacuum to afford 22.3 g of a very dark red oil. This is stirred in 150 ml of n-hexane, whereupon crystallization is initiated. After 2 hours stirring at 0° C. the crystal are filtered off and dried under a water jet vacuum at 40° C. to yield 12.10 g of very dark red crystals. These are recrystallized twice from methylene chloride/methanol. Drying under high vacuum at 35° C. yields 5.07 g of brilliant dark red crystals with a melting point of 134–135° C. and an HPLC purity of 96.5%.

UV/VIS (n-hexane+2% methylene chloride): $\lambda$.max=448 nm ($A^1_1$=1630, $\epsilon$=106300), 473nm (2315, 150900), 503nm (1980, 129300).

EXAMPLE 13
Preparation of racemic plectaniaxanthin dipalmitate

This preparation also starts from racemic plectaniaxanthin, which itself may be prepared according to the procedure described in the first paragraph of the previous example. 5.68 g (10.0 mmol) of rac. plectaniaxanthin (98.6% pure according to HPLC) are suspended in 500 ml of toluene. Then 12.2 g (100 mmol) of 4-dimethylaminopyridine are added to the suspension in one portion. After stirring the mixture for 10 minutes 25.6 g (100 mmol) of palmitic acid are added in one portion followed by a solution of 20.6 g (100 mmol) of N,N'-dicyclohexylcarbodiimide in 50 ml of toluene during 15–20 minutes. The resulting solution is stirred for 20 hours at room temperature and then cooled down to 5° C. while stirring for 20 minutes. The precipitated urea is filtered off and washed twice with 30 ml of cold toluene in each case. The toluene layer is concentrated under reduced pressure on a rotary evaporator at 35° C. to a volume of approx. 90 ml to give a thick paste of crystals. This paste is suspended in 250 ml of n-hexane and stirred for 10 minutes at 0–5° C. The resulting suspension is filtered off and the crystals are washed twice with a little cold n-hexane. The hexane layer is diluted with further n-hexane to a volume of 500–600 ml and washed twice with 200 ml of deionized water at 0° C. in each case, then three times with 200 ml of deionized ice-water in each case, with 3 ml of 3N sulphuric acid and finally five times with 500 ml of deionized ice water in each case until neutral. Then the hexane layer is dried over anhydrous sodium sulphate and concentrated under reduced pressure (rotary evaporator) at 35° C. and thereafter under high vacuum at 40° C. to yield 15.5 g of a very dark red partially crystalline oil. This oil is dissolved in 50 ml of n-hexane/20% diethyl ether and flash-chromatographed on silica gel using 1200 ml of n-hexane/20% diethyl ether and then 1000 ml of diethyl ether as the eluents. After concentration of the fractions containing product there are obtained 12.33 g of a semi-crystalline oil. This oil is dissolved in 60 ml of n-hexane and stirred under argon for 4 days at 4° C.

After filtration the crystals are washed with 100 ml of n-hexane at -50° C. and dried at 35° C. under high vacuum, affording 4.72 g of plectaniaxanthin dipalmitate with a HPLC purity of 97.0%. Since this material still contains some N,N'-dicyclohexylcarbodiimide it is subsequently recrystallized from methylene chloride/n-hexane and methylene chloride/methanol, resulting in 3.77 g of dark red crystals with a HPLC purity of 97.0% and a melting point of 79–81° C.

UV/VIS (n-hexane+2% methylene chloride): $\lambda$.max=447 nm ($A^1_1$=1020, $\epsilon$=106600), 473nm (1440, 150300), 505nm (1230, 128500).

EXAMPLE 14
Carotenoid—Containing Beadlet Composition

| Constituent | Percent by weight |
|---|---|
| Carotene of the invention | 6.0 |
| Ethoxyquin | 1.0 |
| Ascorbyl palmitate | 1.0 |
| Gelatin, Bloom No. 140 | 38.5 |
| Dextrin yellow | 15.7 |
| Crystalline sugar | 15.7 |
| Fluidized corn starch approx. | 22.1 |
| Total | 100.0 |

EXAMPLE 15
Utility of the Carotenoids as Egg Yolk Pigmenters

One of the new carotenoids, namely 5,9,13,18,22-pentamethyl-24-(2,6,6-trimethyl-1-cyclohexen-1-yl)-3,5,7,9,11,13,15,17,19,21,23-tetracosaundecaen-2-one (hereinafter referred to as carotenoid A) was evaluated at a level of 5 ppm in combination with 80% its weight (4 ppm) of ethyl-β-apo-8'-carotenoate ("apo-ester") for its egg yolk pigmenting efficacy in a primary screen with laying hens, and compared with the known pigmenting carotenoid canthaxanthin (the "positive control") under the same conditions, i.e., inter alia at a level of 5 ppm in combination with 4 ppm of apo-ester.

Carotenoid A was formulated as beadlets of the composition given hereinabove in Example 14.

Then the combinations carotenoid A+apo-ester and canthaxanthin +apo-ester and apo-ester alone were incorporated into low-carotenoid basal diets to the extents (inclusion levels) given above (5 ppm+4 ppm in each combination case and 4ppm, respectively). The supplemented basal diets contained in addition 1.10 ppm of lutein and 0.30 ppm of zeaxanthin (a total of 1.40 ppm of xanthophylls) as well as in each case a normal level of supplemental vitamins. The composition of the low-carotenoid basal diet is presented in the following Table 1:

TABLE 1

Composition of low carotenoid basal diet

| Ingredients | Content in weight percent |
|---|---|
| Wheat, ground | 37.00 |
| Oats, ground | 11.00 |
| Rice, broken | 13.00 |
| Soybean meal | 10.00 |
| Fish meal [70% crude protein (CP)] | 5.00 |
| Meat meal, full fat (82% CP) | 1.30 |

TABLE 1-continued

Composition of low carotenoid basal diet

| Ingredients | Content in weight percent |
|---|---|
| Wheat bran | 3.50 |
| Straw meal (NaOH treated) | 2.40 |
| Yeast | 1.00 |
| Hydrolysed fat | 3.60 |
| Ground limestone | 9.55 |
| Salt | 0.20 |
| Methionine premix (25%) | 0.50 |
| Anticaking agent (Diamol ®) | 1.00 |
| Mineral premix (trace elements) | 0.20 |
| Vitamin premix * | 0.75 |
| Calculated content (weight percent) : | 16.80 |
| Crude protein (%) | 11.39 |
| Metabolizable energy (MJ/kg) | 3.78 |
| Crude fibre (%) | 5.77 |
| Crude fat (%) | 4.22 |
| Calcium (%) | 0.43 |
| Phosphorus (%) | |

* consisting of, per kg feed:
Vitamin A 8000 IU, vitamin $D_3$ 1800 IU, vitamin E 60 mg, vitamin $K_3$ 1.3 mg, vitamin C 200 mg, vitamin $B_1$ 4 mg, vitamin $B_2$ 11.8 mg, vitamin $B_6$ 8 mg, vitamin $B_{12}$ 0.04 mg, biotin 0.06 mg, Ca-pantothenate 48 mg, nicotinic acid 104 mg, folic acid 2 mg, choline 1950 mg.

The incorporated carotenoids were checked for content in the feed by HPLC.

The laying hens used in the test were kept in individual cages in a 3-floor battery. 48 "Isa Brown" hens of age 62 weeks were involved, whereby four replicate groups, each of three hens were assigned to each dietary treatment with the combination of carotenoids, with apo-ester alone at an inclusion level of 4 ppm and without a carotenoid (negative control, i.e., basal diet without added test carotenoid).

Before the actual trial the hens were fed the above-indicated low carotenoid basal diet in order to reduce the existing egg yolk pigmentation. Then, during the 3 weeks trial, the hens were fed the same low carotenoid basal diets supplemented with the test carotenoid or containing no such carotenoid (negative control). The feed, in mash form, and water were provided "ad libitum". The laying performance of the hens was monitored once weekly, and the last two eggs per hen were collected and pooled for the laboratory assays (in total, 6 eggs per group).

The pigmenting efficacy was assessed by means of visual scoring (Roche Colour Fan) and reflectance colorimetry (CIE Lab system and CIE-Yxy system), as well as by measurement of carotenoid deposition in the egg yolk. The reflectance measurements were effected using the Xenocolor LS 100 (CIE Lab System) and the Gardner XL colorimeter, and the determined tristimulus values were converted into the CIE system of values of dominant wavelength and spectral saturation [see J. P. Vuilleumier, The "Roche Yolk Colour Fan"—An Instrument for Measuring Yolk Colour, Poultry Science 48, 767–779 (1969)]. The carotenoid deposition measurements, which gave the levels of the test carotenoids in pooled egg yolks, were determined by the same HPLC methods as used for the determination of the carotenoid levels in the diets before feeding, and involved the quantification of the carotenoid originally incorporated in the feed.

The results (average values) are presented in the following tables, viz. Tables 2–4:

TABLE 2

Analytical data in feed and deposition of carotenoids in egg yolks of hens

| Carotenoid (combination); Amount (of each) in ppm | Analytical Content in Feed (mg/kg) | Analytical Content in Egg Yolk (mg/kg) Apo-ester / Other carotenoid |
|---|---|---|
| —(negative control) | * | + |
| Apo-ester/— 4/— | 4.20/— | 16.48 ± 2.12/— |
| Apo-ester/Carotenoid A 4/5 | 3.90/4.80 | 16.20 ± 1.41/9.13 ± 1.21 |
| Apo-ester/Canth. 4/5 | 4.40/5.00 | 15.15 ± 0.83/13.70 ± 0.71 |

* Lutein: 1.10 mg/kg; Zeaxanthin: 0.30 mg/kg; (Xanthophylls: 1.40 mg/kg).
+ Lutein: 1.88 ± 0.05 mg/kg; Zeaxanthin: 0.50 mg/kg; (Xanthophylls: 2.38 ± 0.05 mg/kg).

TABLE 3

Values of reflectance colorimetry (CIE-Lab system) for egg yolks of hens supplemented with carotenoids

| Carotenoid (combination) Amount (of each) in ppm | Lightness L* | Redness a* | Yellowness b* | Hue h*ab | Chroma C*ab |
|---|---|---|---|---|---|
| —(negative control) | 64.97 ± 1.15 | -2.09 ± 0.19 | 38.19 ± 0.56 | 93.14 ± 0.32 | 38.25 ± 0.54 |
| Apo-ester/— 4/— | 61.85 ± 1.37 | 5.37 ± 1.26 | 55.88 ± 1.11 | 84.53 ± 1.21 | 56.15 ± 1.18 |
| Apo-ester/ Carotenoid A 4/5 | 46.31 ± 1.46 | 31.25 ± 1.01 | 34.38 ± 1.66 | 47.71 ± 2.27 | 46.49 ± 0.58 |
| Apo-ester/ Canth. 4/5 | 55.81 ± 0.79 | 21.07 ± 0.51 | 50.15 ± 0.47 | 67.22 ± 0.54 | 54.40 ± 0.47 |

TABLE 4

Values of reflectance colorimetry (CIE-Xxy system) for egg yolks of hens supplemented with carotenoids

| Carotenoid (combination); Amount (of each) in ppm | Visual scoring (Roche Yolk Colour Fan) | Dominant wavelength (nm) | Spectral saturation |
|---|---|---|---|
| —(negative control) | 4.0 | 578.1 ± 0.19 | 0.59 ± 0.02 |
| Apo-ester/— 4/— | 9.0 | 581.8 ± 0.69 | 0.86 ± 0.03 |
| Apo-ester/Carotenoid A 4/5 | >15.0 | 597.9 ± 1.51 | 0.85 ± 0.00 |
| Apo-ester/Canth. 4/5 | 13.0 | 587.9 ± 0.38 | 0.89 ± 0.00 |

The results show that Carotenoid A [5,9,13,18,22-pentamethyl-24-(2,6,6-trimethyl-1-cyclohex-1-yl)-3,5,7,9,11,13,15,17,19,21,23-tetracosaundecaen-2-one] was deposited in considerable quantity in the egg yolk (Table 2: 67% of the canthaxanthin concentration), as a result of which this carotenoid improved very significantly the redness of the egg yolks (Table 3). Accordingly the respective colour hue (Table 3) was more favourable than that of canthaxanthin. Due to a relatively low portion of yellowness with carotenoid A, chroma of canthaxanthin was superior to that of carotenoid A. These findings were entirely confirmed by the values for dominant wavelength and colour fan (Table 4), indicating that carotenoid A has a much higher pigmenting potency than canthaxanthin and is an excellent red pigmenting agent for egg yolks.

EXAMPLE 16

Utility of the Carotenoids as Egg Yolk Pigmenters

A further new carotenoid, namely 5,9,13,17,22,26-hexamethyl-28-(2,6,6-trimethyl-1-cyclohexen-1-yl)-3,5,7,9,11,13,15,17,19,21,23,25,27-octacosatridecaen-2-one [or (16'-torulenylidene)acetone; hereinafter referred to as carotenoid B] was evaluated at levels of 5 ppm, 2.5 ppm, 1.5 ppm and 0.75 ppm in combination with 4 ppm of ethyl β-apo-8'-carotenoate ("apo-ester") for its egg yolk pigmenting efficacy in a primary screen with laying hens, and compared with the known pigmenting carotenoids canthaxanthin (canth.) and 2'-dehydroplectaniaxanthin (2'-DHP) at a dose level of 5 ppm and 0.85 ppm, respectively, in combination with 4 ppm of apo-ester under the same conditions. Control treatments involved diets with no carotenoid supplementation and with 4 ppm of apo-ester as the only carotenoid.

Carotenoid B was formulated as beadlets of the composition given hereinabove in Example 14.

Then the combinations carotenoid B+apo-ester, canthaxanthin+apo-ester and 2'-dehydroplectaniaxanthin+apo-ester, and apo-ester as the sole supplementing carotenoid, were incorporated into low-carotenoid basal diets to the extents (levels) given above (5/2.5/1.5/0.75 ppm+4 ppm; 5 ppm+4 ppm; 0.85 ppm+4 ppm; and 4 ppm, respectively).

The composition of the low-carotenoid basal diet was essentially the same as that presented in Table 1 in Example 15, but the vitamin premix (also of 0.75 weight percent content) was of somewhat different constitution, as follows:

Per kg feed: Vitamin A 10000 IU, vitamin $D_3$ 2000 IU, vitamin E 71 mg, vitamin $K_3$ 2.6 mg, vitamin C 200 mg, vitamin $B_1$ 4 mg, vitamin $B_2$ 12.1 mg, vitamin $B_6$ 8 mg, vitamin $B_{12}$ 0.04 mg, biotin 0.06 mg, Ca-pantothenate 48 mg, nicotinic acid 104 mg, folic acid 2 mg, choline 1719 mg.

Furthermore, the supplemental basal diets contained in addition 1.00 mg/kg of lutein, 0.40 mg/kg of zeaxanthin and 1.40 mg/kg of xanthophylls (first trial) or 0.30 mg/kg of lutein,<0.10 mg/kg of zeaxanthin and 0.30 mg/kg of xanthophylls (second trial).

The incorporated carotenoids were checked for content in the feed by HPLC.

The laying hens used in the two trials (1 and 2) which were conducted were kept in individual cages in a 3-floor battery. "Isa Brown" hens of age 35 weeks (trial 1) or 40 weeks (trial 2) were involved, whereby four replicate groups, each of three hens, were assigned to each dietary treatment with the combination of two carotenoids, with apo-ester alone at an inclusion level of 4 ppm and without a carotenoid (negative control, i.e., basal diet without added test carotenoid).

The two trials were conducted, and the pigmenting efficacies assessed, in the same way as described for the trial and assessment reported in Example 15 hereinbefore, and the results (average values) are presented in the following tables, viz. Tables 5.1 to 8.2:

TABLE 5.1

Analytical data in feed and deposition of carotenoids in egg yolks of hens (Trial 1)

| Carotenoid (combination); Amount (of each) in ppm | Analytical Content in Feed (mg/kg) | Analytical Content in Egg Yolk (mg/kg) |
|---|---|---|
| —(negative control) | —[1] | —[2] |
| Apo-ester/— 4/— | 4.10/— | 11.93 ± 0.68/— |
| Apo-ester/Carotenoid B 4/5.00 | 3.90/5.60 | 13.10 ± 0.55/ 3.48 ± 0.15 |
| Apo-ester/Carotenoid B 4/2.50 | 4.00/2.90 | 13.73 ± 0.39/ 2.33 ± 0.05 |
| Apo-ester/Canth. 4/5.00 | 3.80/6.70 | 12.13 ± 0.59/ 11.65 ± 0.71 |
| Apo-ester/2'-DHP 4/0.85 | 4.50/1.00 | 11.98 ± 0.34/ 1.93 ± 0.19 |

[1]Lutein: 1.00 mg/kg; zeaxanthin: 0.40 mg/kg; (xanthophylls: 1.40 mg/kg).
[2]Lutein: 1.25 ± 0.17 mg/kg; zeaxanthin: 0.18 ± 0.05 mg/kg; (xanthophylls: 1.43 ± 0.21 mg/kg).

TABLE 5.2

Analytical data in feed and deposition of carotenoids in egg yolks of hens (Trial 2)

| Carotenoid (combination); Amount (of each) in ppm | Analytical Content in Feed (mg/kg) | Analytical Content in Egg Yolk (mg/kg) |
|---|---|---|
| —(negative control) | —[3] | —[4] |
| Apo-ester/— 4/— | 4.00/— | 13.80 ± 1.78/— |
| Apo-ester/Carotenoid B 4/1.50 | 3.60/1.50 | 12.98 ± 0.25/ 1.38 ± 0.13 |
| Apo-ester/Carotenoid B 4/0.75 | 4.00/0.85 | 12.88 ± 0.81/ 0.70 ± 0.08 |
| Apo-ester/Canth. 4/5.00 | 3.90/5.20 | 14.45 ± 0.42/ 12.90 ± 0.54 |
| Apo-ester/2'-DHP 4/0.85 | 4.70/0.70 | 15.80 ± 1.09/ 2.38 ± 0.13 |

[3]Lutein: 0.30 mg/kg; zeaxanthin: <0.10 mg/kg; (xanthophylls: 0.30 mg/kg).
[4]Lutein: 1.33 ± 0.13 mg/kg; zeaxanthin: 0.13 ± 0.05 mg/kg; (xanthophylls: 1.45 ± 0.17 mg/kg).

TABLE 6.1

Values of reflectance colorimetry (CIE-Lab system) for egg yolks of hens supplemented with carotenoids (Trial 1)

| Carotenoid (combination) Amount (of each) in ppm | Lightness L* | Redness a* | Yellowness b* | Colour Hue h*ab | Chroma C*ab |
|---|---|---|---|---|---|
| —(negative control) | 66.44 ± 0.84 | −4.31 ± 0.12 | 35.21 ± 0.91 | 96.98 ± 0.36 | 35.47 ± 0.90 |
| Apo-ester/— 4/— | 62.30 ± 0.53 | 3.65 ± 0.46 | 55.67 ± 1.02 | 86.26 ± 0.41 | 55.79 ± 1.04 |
| Apo-ester/ Carotenoid B 4/5.00 | 45.90 ± 0.56 | 26.76 ± 0.54 | 31.74 ± 0.34 | 49.86 ± 0.58 | 41.52 ± 0.48 |
| Apo-ester/ Carotenoid B 4/2.50 | 48.80 ± 0.50 | 22.84 ± 0.14 | 36.05 ± 0.47 | 57.65 ± 0.43 | 42.67 ± 0.37 |
| Apo-ester/ Canth. 4/5.00 | 55.12 ± 0.96 | 21.02 ± 0.74 | 49.55 ± 0.95 | 67.01 ± 0.99 | 53.83 ± 0.78 |
| Apo-ester/ 2'-DHP 4/0.85 | 54.82 ± 0.54 | 16.14 ± 0.86 | 43.92 ± 1.02 | 69.83 ± 0.87 | 46.80 ± 1.13 |

TABLE 6.2

Values of reflectance colorimetry (CIE-Lab system) for egg yolks of hens supplemented with carotenoids (Trial 2)

| Carotenoid (combination) Amount (of each) in ppm | Lightness L* | Redness a* | Yellowness b* | Colour Hue h*ab | Chroma C*ab |
|---|---|---|---|---|---|
| —(negative control) | 67.20 ± 0.83 | −4.01 ± 0.16 | 30.51 ± 1.39 | 97.50 ± 0.42 | 30.78 ± 1.38 |
| Apo-ester/—4/— | 62.95 ± 0.71 | 3.72 ± 0.55 | 54.22 ± 0.44 | 86.08 ± 0.55 | 54.35 ± 0.47 |
| Apo-ester/Carotenoid B 4/1.50 | 54.25 ± 0.66 | 17.25 ± 0.16 | 41.65 ± 1.40 | 67.49 ± 0.68 | 45.08 ± 1.30 |
| Apo-ester/Carotenoid B 4/0.75 | 57.13 ± 0.61 | 12.22 ± 0.60 | 45.98 ± 0.80 | 75.12 ± 0.74 | 47.58 ± 0.79 |
| Apo-ester/Canth. 4/5.00 | 56.56 ± 0.56 | 20.03 ± 0.53 | 49.82 ± 0.89 | 68.10 ± 0.30 | 53.70 ± 0.99 |
| Apo-ester/2'-DHP 4/0.85 | 56.01 ± 0.80 | 16.10 ± 0.39 | 44.29 ± 1.03 | 70.03 ± 0.33 | 47.12 ± 1.06 |

TABLE 7.1

Values of reflectance colorimetry (CIE-Xxy system) for egg yolks of hens supplemented with carotenoids (Trial 1)

| Carotenoid (combination); Amount (of each) in ppm | Visual scoring (Roche Yolk Colour Fan) | Dominant wavelength (nm) | Spectral saturation |
|---|---|---|---|
| —(negative control) | 3.0 ± 0 | 578.3 ± 0.1 | 0.53 ± 0.01 |
| Apo-ester/—4/— | 8.0 ± 0 | 582.0 ± 0.2 | 0.83 ± 0.01 |
| Apo-ester/Carotenoid B 4/5.00 | 15.0 ± 0 | 594.3 ± 0.3 | 0.78 ± 0.01 |
| Apo-ester/Carotenoid B 4/2.50 | 15.0 ± 0 | 591.2 ± 0.1 | 0.80 ± 0.01 |
| Apo-ester/Canth. 4/5.00 | 13.0 ± 0 | 588.8 ± 0.4 | 0.90 ± 0.01 |
| Apo-ester/2'-DHP 4/0.85 | 13.0 ± 0 | 587.2 ± 0.4 | 0.84 ± 0.01 |

TABLE 7.2

Values of reflectance colorimetry (CIE-Xxy system) for egg yolks of hens supplemented with carotenoids (Trial 2)

| Carotenoid (combination); Amount (of each) in ppm | Visual scoring (Roche Yolk Colour Fan) | Dominant wavelength (nm) | Spectral saturation |
|---|---|---|---|
| —(negative control) | 2.0 ± 0 | 578.0 ± 0.2 | 0.47 ± 0.02 |
| Apo-ester/—4/— | 8.0 ± 0 | 582.0 ± 0.2 | 0.82 ± 0.01 |
| Apo-ester/Carotenoid B 4/1.50 | 13.0 ± 0 | 587.8 ± 0.2 | 0.82 ± 0.01 |
| Apo-ester/Carotenoid B 4/0.75 | 12.0 ± 0 | 585.4 ± 0.3 | 0.83 ± 0.01 |
| Apo-ester/Canth. 4/5.00 | 13.0 ± 0 | 588.2 ± 0.2 | 0.89 ± 0.01 |
| Apo-ester/2'-DHP 4/0.85 | 13.0 ± 0 | 587.1 ± 0.2 | 0.84 ± 0.01 |

TABLE 8.1

Production data of hens supplemented with carotenoids (Trial 1)

| Carotenoid (combination); Amount (of each) in ppm | No of eggs/group [5]: total/intact | Egg production (%)[6] | Feed intake/group (g) | Feed intake/egg (g)[6] | Mean egg weight (g)[7] | Egg mass (g)[8] | Feed conversion |
|---|---|---|---|---|---|---|---|
| —(negative control) | 61/60 | 96.0 | 6285 | 104 | 58 | 3512 | 1.79 |
| Apo-ester/—4/— | 61/61 | 97.2 | 6696 | 109 | 59 | 3621 | 1.85 |
| Apo-ester/Carotenoid B 4/5.00 | 62/60 | 97.6 | 6870 | 112 | 61 | 3722 | 1.85 |
| Apo-ester/Carotenoid B 4/2.50 | 58/57 | 92.5 | 6624 | 114 | 60 | 3490 | 1.90 |
| Apo-ester/Canth. 4/5.00 | 56/55 | 88.5 | 6644 | 122 | 59 | 3307 | 2.06 |
| Apo-ester/2'-DHP 4/0.85 | 59/57 | 94.1 | 6791 | 115 | 61 | 3589 | 1.90 |

[5] The total number consists of all laid, including broken, eggs, of which the intact eggs are the usable ones.
[6] Based on the total number of laid, including broken, eggs.
[7] Based on the number of intact (i.e., usable) eggs.
[8] These figures include the (extrapolated) egg mass of broken eggs (adjusted according to the total number of eggs).

TABLE 8.2

Production data of hens supplemented with carotenoids (Trial 2)

| Carotenoid (combination); Amount (of each) in ppm | No of eggs/group [5]: total/intact | Egg production (%)[6] | Feed intake/group (g) | Feed intake/egg (g)[6] | Mean egg weight (g)[7] | Egg mass (g)[8] | Feed conversion |
|---|---|---|---|---|---|---|---|
| —(negative control) | 59/59 | 93.3 | 6137 | 104 | 59 | 3484 | 1.76 |
| Apo-ester/—4/— | 57/56 | 90.5 | 6481 | 114 | 61 | 3494 | 1.85 |
| Apo-ester/Carotenoid B 4/1.50 | 59/57 | 93.3 | 6718 | 115 | 62 | 3618 | 1.86 |
| Apo-ester/Carotenoid B 4/0.75 | 51/50 | 81.4 | 6503 | 129 | 63 | 3211 | 2.05 |
| Apo-ester/Canth. 4/5.00 | 59/54 | 93.7 | 6966 | 119 | 64 | 3783 | 1.85 |
| Apo-ester/2'-DHP 4/0.85 | 59/57 | 94.1 | 6702 | 113 | 61 | 3603 | 1.86 |

[5], [6], [7] and [8]:See explanations at end of Table 8.1

The results show inter alia that the analytical concentrations of the carotenoids in the feeds were in an acceptable range for the target levels, whereby a tendency for slightly higher values was observed, particularly for canthaxanthin in trial 1 (see Table 5.1). The concentrations of apo-ester in the egg yolks ranged between about 12 and about 14 mg/kg (trial 1) or between about 13 and about 16 mg/kg (trial 2) and were not influenced by the other carotenoid present in the combinations. Carotenoid B was deposited in considerable quantity in the egg yolk (Tables 5.1 and 5.2). As regards the reflectance colorimetry results (Tables 6 and 7), the higher dose levels of carotenoid B tested (5.00 and 2.50 ppm in trial 1) caused a strong red pigmentation, so that this carotenoid was also tested, in trial 2,at the lower dose levels 1.50 and 0.75 ppm. Carotenoid B exhibited at the dose level 1.50 ppm a pigmentation level comparable with that of 2'-DHP and a slightly lower colour hue (Tables 6.2 and 7.2) whereas the pigmentation obtained with the lower dose 0.75 ppm was weaker. In comparison to canthaxanthin in the pertinent trial 2 the values for redness and colour saturation (chroma) were lower.

From Tables 8.1 and 8.2 it can be seen that although variations occurred in the production data of the laying hens the egg production was not influenced by the various carotenoid treatments.

In conclusion, carotenoid B [5,9,13,17,22,26-hexamethyl-28-(2,6,6-trimethyl-1-cyclohexen-1-yl)-3,5,7,9,11,13,15,17,19,21,23,25,27-octacosatridecaen-2-one, or (16'-torulenylidene)acetone] is a carotenoid with a good deposition in egg yolk and a high red pigmenting potential.

EXAMPLE 17

Utility of the Carotenoids as Egg Yolk Pigmenters

Two further new carotenoids, namely 1',2'-dihydro-17'-nor-beta-χ-caroten-2'-one (hereinafter referred to as carotenoid C) and (all E)-2,9,1 3,17,22,26-hexamethyl-28-(2,6,6-trimethyl-cyclohex-1-enyl)-octacosa-2,7,9,11,13,15,17,19,21,23,25,27-dodecaen-6-one [hereafter referred to as carotenoid D) were evaluated at levels of 5.0 ppm and 2.5 ppm (carotenoid C) and 5.0 ppm 2.0 ppm and 0.8 ppm (carotenoid D) in combination with 4 ppm of ethyl β-apo-8'-carotenoate ("apo-ester") for its egg yolk pigmenting efficacy in a primary screen with laying hens, and compared with the known pigmenting carotenoids canthaxanthin and 2'-dehydroplectaniaxanthin (2'-DHP) at dose levels of 5.0 ppm and 2.5 ppm (canthaxanthin) and 0.85 ppm (2'-DHP) in combination with 4 ppm of apo-ester under the same conditions. Control treatments involved diets with no carotenoid supplementation and with 4 ppm of apo-ester as the only carotenoid.

Both carotenoids C and D were formulated as beadlets of the composition given hereinabove in Example 14.

Then the combinations carotenoid C+apo-ester, carotenoid D+apo-ester, canthaxanthin+apo-ester and 2'-dehydroplectaniaxanthin 5 +apo-ester, and apo-ester as the sole supplementing carotenoid, were incorporated into low-carotenoid basal diets to the extents (levels) given above (5/2.5 ppm+4 ppm; 5/2/0.8 ppm+4 ppm; 5/2.5 ppm+4 ppm; 0.85 ppm+4 ppm; and 4 ppm, respectively).

The composition of the low-carotenoid basal diet was essentially the same as that presented in Table 1 in Example 15,but the vitamin premix (also of 0.75 weight percent content) was of somewhat different constitution, as follows:

Per kg feed: Vitamin A 10000 IU, vitamin $D_3$ 2000 IU, vitamin E 71 mg, vitamin $K_3$ 2.6 mg, vitamin C 200 mg, vitamin $B_1$ 4 mg, vitamin $B_2$ 12.1 mg, vitamin $B_6$ 8 mg,vitamin $B_{12}$ 0.04 mg, biotin 0.06 mg, Ca-pantothenate 48 mg, nicotinic acid 104 mg, folic acid 2 mg, choline 1719 mg.

Furthermore, the supplemental basal diets contained in addition 0.60 mg/kg of lutein and 0.10 mg/kg of zeaxanthin (0.70 mg/kg of xanthophylls).

The incorporated carotenoids were checked for content in the feed by HPLC.

The laying hens used in the trial which was conducted were kept in individual cages in a 3-floor battery. "Isa Brown" hens of age 49 weeks were involved, whereby four replicate groups, each of three hens were assigned to each dietary treatment with the combination of two carotenoids, with apo-ester alone at an inclusion level of 4 ppm and without a carotenoid (negative control, i.e., basal diet without added test carotenoid).

The trial was conducted, and the pigmenting efficacies assessed, in the same way as described for the trial and assessment reported in Example 15 hereinbefore, and the results (average values) are presented in the following tables, viz. Tables 9–12:

TABLE 9

Analytical data in feed and deposition of carotenoids in egg yolks of hens

| Carotenoid (combination); Amount (of each) in ppm | Analytical Content in Feed (mg/kg) | Analytical Content in Egg Yolk (mg/kg) |
|---|---|---|
| —(negative control) | —[9] | —[10] |
| Apo-ester/— 4/— | 4.60/— | 15.75 ± 0.64/— |
| Apo-ester/Carotenoid C 4/5.00 | 4.20/5.20 | 17.60 ± 1.37/ 8.53 ± 0.72 |
| Apo-ester/Carotenoid C 4/2.50 | 4.20/2.60 | 16.73 ± 1.42/ 4.75 ± 0.47 |
| Apo-ester/Carotenoid D 4/5.00 | 4.10/5.00 | 15.13 ± 0.87/ 1.20 ± 0.12 |
| Apo-ester/Carotenoid D 4/2.00 | 4.40/2.20 | 15.88 ± 0.21/ 1.05 ± 0.17 |
| Apo-ester/Carotenoid D 4/0.80 | 4.00/1.00 | 15.58 ± 0.93/ 0.78 ± 0.13 |
| Apo-ester/Canth. 4/5.00 | 4.30/5.70 | 15.90 ± 0.68/ 15.15 ± 0.78 |
| Apo-ester/Canth. 4/2.50 | 3.90/2.70 | 15.05 ± 0.62/ 7.20 ± 0.37 |
| Apo-ester/2'-DHP 4/0.85 | 4.60/0.80 | 15.08 ± 1.38/ 2.05 ± 0.34 |

[9]Lutein: 0.60 mg/kg; zeaxanthin: 0.10 mg/kg; (xanthophylls: 0.70 mg/kg).
[10]Lutein: 0.90 ± 0.08 mg/kg; zeaxanthin: <0.10 mg/kg; (xanthophylls: 0.95 ± 0.10 mg/kg).

TABLE 10

Values of reflectance colorimetry (CIE-Lab system) for egg yolks of hens supplemented with carotenoids

| Carotenoid (combination) Amount (of each) in ppm | Lightness L* | Redness a* | Yellowness b* | Colour Hue h*ab | Chroma C*ab |
|---|---|---|---|---|---|
| —(negative control) | 66.26 ± 0.54 | -4.04 ± 0.25 | 35.24 ± 1.11 | 96.54 ± 0.46 | 35.47 ± 1.10 |
| Apo-ester/— 4/— | 62.28 ± 0.79 | 4.45 ± 0.32 | 56.01 ± 0.87 | 85.46 ± 0.37 | 56.19 ± 0.85 |
| Apo-ester/ Carotenoid C 4/5.00 | 48.33 ± 1.22 | 31.53 ± 0.87 | 37.27 ± 1.83 | 49.74 ± 1.84 | 48.83 ± 1.28 |
| Apo-ester/ Carotenoid C 4/2.50 | 51.04 ± 0.94 | 26.21 ± 0.50 | 40.34 ± 0.69 | 56.98 ± 0.80 | 48.11 ± 0.53 |
| Apo-ester/ Carotenoid D 4/5.00 | 57.70 ± 0.18 | 12.46 ± 1.06 | 48.30 ± 0.89 | 75.55 ± 1.09 | 49.89 ± 0.99 |
| Apo-ester/ Carotenoid D 4/2.00 | 59.72 ± 1.12 | 11.06 ± 1.31 | 49.89 ± 1.24 | 77.50 ± 1.46 | 51.11 ± 1.26 |
| Apo-ester/ Carotenoid D 4/0.80 | 59.77 ± 0.35 | 9.57 ± 1.07 | 51.05 ± 0.49 | 79.39 ± 1.17 | 51.95 ± 0.53 |
| Apo-ester/ Canth. 4/5.00 | 54.86 ± 1.15 | 21.44 ± 0.60 | 49.11 ± 1.46 | 66.41 ± 0.74 | 53.58 ± 1.42 |
| Apo-ester/ Canth. 4/2.50 | 57.96 ± 0.92 | 15.42 ± 0.36 | 51.73 ± 0.48 | 73.39 ± 0.50 | 53.98 ± 0.37 |
| Apo-ester/ 2'-DHP 4/0.85 | 54.61 ± 1.03 | 17.54 ± 0.70 | 44.64 ± 0.72 | 68.55 ± 1.10 | 47.97 ± 0.41 |

TABLE 11

Values of reflectance colorimetry (CIE-Xxy system) for egg yolks of hens supplemented with carotenoids

| Carotenoid (combination); Amount (of each) in ppm | Visual scoring (Roche Yolk Colour Fan) | Dominant wavelength (nm) | Spectral saturation |
|---|---|---|---|
| —(negative control) | 2.0 ± 0 | 578.4 ± 0.2 | 0.53 ± 0.01 |
| Apo-ester/—4/— | 8.0 ± 0 | 582.1 ± 0.1 | 0.84 ± 0.01 |
| Apo-ester/Carotenoid C 4/5.00 | >15.0 | 595.3 ± 0.8 | >0.84[11] |
| Apo-ester/Carotenoid C 4/2.50 | 15.0 ± 0 | 592.0 ± 0.4 | >0.84[11] |
| Apo-ester/Carotenoid D 4/5.00 | 12.0 ± 0 | 585.4 ± 0.5 | 0.85 ± 0.01 |
| Apo-ester/Carotenoid D 4/2.00 | 11.0 ± 0 | 584.6 ± 0.6 | 0.86 ± 0.02 |
| Apo-ester/Carotenoid D 4/0.80 | 11.0 ± 0 | 584.1 ± 0.5 | 0.85 ± 0.01 |
| Apo-ester/Canth. 4/5.00 | 13.0 ± 0 | 589.9 ± 0.3 | 0.90 ± 0.01 |
| Apo-ester/Canth. 4/2.50 | 11.0 ± 0 | 586.4 ± 0.2 | 0.89 ± 0.00 |
| Apo-ester/2'-DHP 4/0.85 | 14.0 ± 0 | 587.7 ± 0.5 | 0.84 ± 0.00 |

[11]Dominant wavelength too high for an exact spectral saturation to be quantified.

TABLE 12

Production data of hens supplemented with carotenoids

| Carotenoid (combination); Amount (of each) in ppm | No of eggs/group[5]: total/intact | Egg production (%)[6] | Feed intake/group (g) | Feed intake/egg (g)[6] | Mean egg weight (g)[7] | Egg mass (g)[8] | Feed conversion |
|---|---|---|---|---|---|---|---|
| —(negative control) | 54/54 | 83.3 | 6151 | 115 | 61 | 3291 | 1.87 |
| Apo-ester/—4/— | 55/54 | 83.3 | 6368 | 116 | 60 | 3270 | 1.95 |
| Apo-ester/Carotenoid C 4/5.00 | 47/47 | 75.0 | 5989 | 130 | 61 | 2865 | 2.14 |
| Apo-ester/Carotenoid C 4/2.50 | 52/50 | 82.9 | 6415 | 124 | 62 | 3219 | 2.01 |
| Apo-ester/Carotenoid D 4/5.00 | 55/52 | 86.9 | 6475 | 119 | 61 | 3360 | 1.94 |
| Apo-ester/Carotenoid D 4/2.00 | 54/54 | 85.7 | 6321 | 117 | 62 | 3328 | 1.90 |
| Apo-ester/Carotenoid D 4/0.80 | 52/50 | 81.7 | 6202 | 121 | 63 | 3265 | 1.90 |
| Apo-ester/Canth. 4/5.00 | 53/51 | 84.5 | 6662 | 125 | 63 | 3363 | 1.99 |
| Apo-ester/Canth. 4/2.50 | 57/56 | 89.7 | 6331 | 112 | 60 | 3409 | 1.86 |
| Apo-ester/2'-DHP 4/0.85 | 51/50 | 81.0 | 6184 | 121 | 62 | 3163 | 1.96 |

[5) 6) 7) and 8)]:See explanations at end of Table 8.1.

The results show that the analytical concentrations of the carotenoids in the feeds were in an acceptable range for the target levels. The test and comparison (canthaxanthin and 2'-DHP) carotenoids were deposited in the egg yolk, and it was observed that the concentration increased with increasing dose levels. Compared with canthaxanthin the concentrations of carotenoids C and D in the egg yolk were lower (decreasing values from carotenoid C to carotenoid D). According to the results presented in Tables 10 and 11 carotenoid C showed high red pigmenting properties reflected in high values for redness and low values for colour hue. The red pigmentation was stronger than that of canthaxanthin. Carotenoid C had lower values for lightness, yellowness and chroma than canthaxanthin, attributable to the stronger pigmentation. Carotenoid D also caused a significant red pigmentation of the egg yolk, with increasing redness and decreasing colour hue as the dose was increased, but the pigmentation efficacy was lower than for canthaxanthin and 2'-DHP. In respect of yellowness, carotenoid D had similar values to canthaxanthin and higher values than those of 2'-DHP, and the chroma values were between those of these comparison carotenoids. From Table 12 it can be seen that although variations occurred in the production data of the laying hens the egg production was not influenced by the various carotenoid treatments.

In conclusion, carotenoid C (1',2'-dihydro-17'-nor-beta-χ-caroten-2'-one) has a high potential for red pigmentation of egg yolk, and carotenoid D [(all E)-2,9,13,17,22,26-hexamethyl-28-(2,6,6-trimethyl-cyclohex-1-enyl)-octacosa-2,7,9,11,13,15,17,19,21,23,25,27-dodecaen-6-one] also causes considerable pigmentation, albeit somewhat lower than that caused by canthaxanthin and 2'-DHP.

We claim:

1. A beadlet comprising a matrix of gelatin and carbohydrate having dispersed therein a pharmaceutically acceptable antioxidant and a carotenoid of the formula:

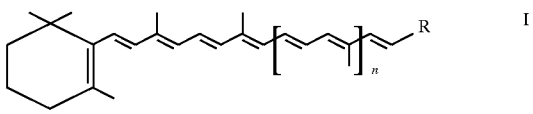

wherein

R is a group (b) or (c):

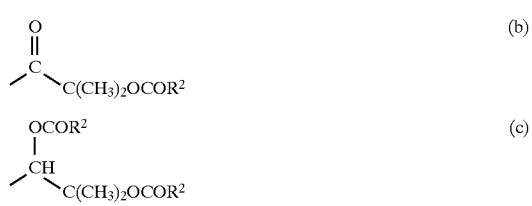

in each of which $R^2$ is $C_{1-15}$-akyl, and n is zero or an integer from 1 to 4, wherein said carotenoid is present in said beadlet in an amount from 1 to 20 percent by weight of said beadlet.

2. The beadlet of claim 1 wherein R is group (b).

3. The beadlet of claim 2 wherein n is an integer from 1 to 4 and $R^2$ is $C_{1-15}$-alkyl.

4. The beadlet of claim 3 wherein n is 3.

5. The beadlet of claim 4 wherein $R^2$ is methyl and said carotenoid is 2'-dehydroplectaniaxanthin acetate.

6. A feed composition for poultry, fish or crustacea comprising a poultry, fish or crustacea feed and a carotenoid of the formula:

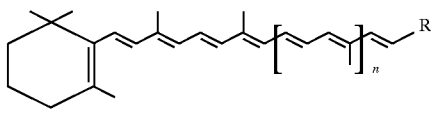

wherein

R is a group (b) or (c)

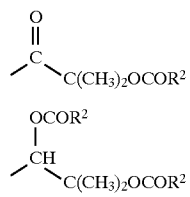

in each of which $R^2$ is $C_{1-15}$-alkyl, and n is zero or an integer 1 to 4, wherein said carotenoid is present in said composition in an amount effective to pigment the egg yolk, meat, integuments and subcutaneous fat of the poultry or to pigment the meat and integuments of the fish and crustacea to which said composition is fed.

7. The feed composition of claim 6, wherein the amount of said carotenoid in said composition is in the range 0.1 ppm to 150 ppm based on the total weight of said composition.

8. The feed composition of claim 7 wherein R is group (b).

9. The feed composition of claim 8 wherein n is an integer from 1 to 4 and $R^2$ is $C_{1-15}$-alkyl.

10. The feed composition of claim 9 wherein n is 3.

11. The feed composition of claim 10 wherein $R^2$ is methyl and said carotenoid is 2'-dehydroplectaniaxanthin acetate.

12. The feed composition of claim 11 wherein said feed is a poultry feed and the total concentration of said carotenoid in said composition is in the range from 0.25 ppm to 20 ppm based upon the total weight of said composition.

13. The feed composition of claim 11 wherein said feed is a fish or crustacea feed and the total concentration of said carotenoid in said composition is in the range from 2.5 ppm to 150 ppm based upon the total weight of said composition.

14. The feed composition of claim 10 wherein $R^2$ is pentadecyl and said carotenoid is 2'-dehydroplectaniaxanthin palmitate.

15. The feed composition of claim 14 wherein said feed is a poultry feed and the total concentration of said carotenoid in said composition is in the range from 0.25 ppm to 20 ppm based upon the total weight of said composition.

16. The feed composition of claim 14 wherein said feed is a fish or crustacea feed and the total concentration of said carotenoid in said composition is in the range from 2.5 ppm to 150 ppm based upon the total weight of said composition.

17. A composition which when added to a poultry, fish or crustacea feed provides a combination of nutrients and pharmaceutically active substances for ingestion by said poultry, fish or crustacea, wherein said composition comprises a beadlet comprising a matrix of gelatin and carbohydrate and having dispersed therein a pharmaceutically acceptable antioxidant and a carotenoid of the formula:

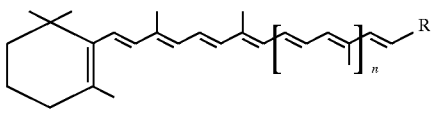

wherein

R is a group (b) or (c)

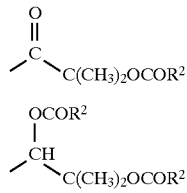

in each of which $R^2$ is $C_{1-15}$-alkyl, and n is zero or an integer 1 to 4, admixed with poultry, fish or crustacea nutrients or pharmaceutically active substances, wherein said carotenoid is present in said composition in an amount from 0.001 to 15 percent by weight of said composition.

18. The composition of claim 17 wherein R is group (b).

19. The composition of claim 18 wherein n is an integer from 1 to 4 and $R^2$ is $C_{1-15}$-alkyl.

20. The composition of claim 19 wherein n is 3.

21. The composition of claim 20 wherein $R^2$ is methyl and said carotenoid is 2'-dehydroplectaniaxanthin acetate.

22. A carotenoid of the formula:

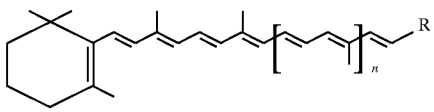

wherein R is a group (b)

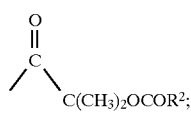

$R^2$ is $C_{1-15}$-alkyl; and n is zero or an integer from 1 to 4.

23. The carotenoid of claim 22 wherein n is 3.

24. The carotenoid of claim 22 wherein $R^2$ is methyl and said carotenoid is 2'-dehydroplectaniaxanthin acetate.

25. The carotenoid of claim 22 wherein $R^2$ is pentadecyl and said carotenoid is 2'-dehydroplectaniaxanthin palmitate.

26. A method of pigmenting the egg yolk, integuments and subcutaneous fat of poultry, and the meat and integuments of fish and crustacea, said method comprising feeding said poultry, fish or crustacea a feed composition for poultry, fish or crustacea comprising a poultry, fish or crustacea feed and a carotenoid of the formula:

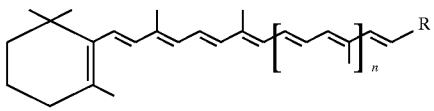

wherein
R is a group (b) or (c)

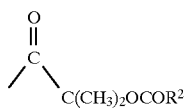 (b)

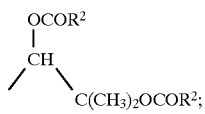 (c)

in each of which $R^2$ is $C_{1-15}$-alkyl; and n is zero or an integer 1 to 4, wherein said carotenoid is present in said composition in an amount effective to pigment the egg yolk meat, integuments and subcutaneous fat of the poultry or to pigment the meat and integuments of the fish and crustacea to which said composition is fed.

27. The method of claim 26, wherein the amount of said carotenoid in said composition is in the range 0.1 ppm to 150 ppm based on the total weight of said composition.

28. The method of claim 26 wherein said feed is a poultry feed and the amount of said carotenoid in said composition is in the range from 0.25 ppm to 20 ppm based upon the total weight of said composition.

29. The method of claim 26 wherein said feed is a fish or crustacea feed and the amount of said carotenoid in said composition is in the range from 2.5 ppm to 150 ppm based upon the total weight of said composition.

30. The method of claim 26 wherein n is 4.

* * * * *